United States Patent [19]

Kimoto et al.

[11] Patent Number: 4,628,260
[45] Date of Patent: Dec. 9, 1986

[54] EDDY CURRENT DEFECT-DETECTING SYSTEM FOR DETERMINING AN INNER OR OUTER DEFECT AND ITS DEPTH IN METAL TUBES

[76] Inventors: Sanshiro Kimoto, 1-4-32 Nakayamahigashi, Higashi-ku, Hiroshima-shi, Hiroshima-ken; Hisao Kokubo, 4-8-16 Tatsumidaihigashi, Ichihara-shi, Chiba-ken; Yasunobu Yamabayashi, 1-1 Yuushuudaihigashi, Ichihara-shi, Chiba-ken; Kenichi Hidejima, 3-2 Yuushuudaihigashi, Ichihara-shi, Chiba-ken, all of Japan

[21] Appl. No.: 543,357

[22] Filed: Oct. 19, 1983

[30] Foreign Application Priority Data

Oct. 21, 1982 [JP] Japan ................................ 57-185696

[51] Int. Cl.[4] ..................... G01N 27/72; G01N 27/82; G01R 33/12
[52] U.S. Cl. ..................................... 324/220; 324/233
[58] Field of Search .............................. 324/219-221, 324/227, 233, 236-238; 364/550, 551, 580

[56] References Cited

U.S. PATENT DOCUMENTS 3,528,003  9/1970  Förster .............................. 324/227
3,848,182  11/1974 Gerner et al. ...................... 324/233
4,188,577  2/1980  Mhatre et al. ..................... 324/233

Primary Examiner—Ernest F. Karlsen
Assistant Examiner—Walter E. Snow
Attorney, Agent, or Firm—Pahl, Lorusso & Loud

[57] ABSTRACT

An eddy current defect-detecting system for a metal tube comprises a detector including test coils movable axially through the metal tube for detecting as an impedance variation a variation in an eddy current produced due to a defect present in the metal tube, an oscillator for exciting the detector at a high frequency, a phase adjuster responsive to an oscillated output from the oscillator for adjusting the phase of the oscillated output to produce a first control signal, a phase shifter responsive to the first control signal from the phase adjuster for issuing a second control signal which is 90° out of phase with the first control signal, two phase detectors for producing a first defect signal by effecting first phase detection on an output signal from the detector with the first control signal and a second defect signal by effecting second phase detection on the output signal from the detector with the second control signal, an arithmetic processing unit for electrically reading amplitudes of the first and second defect signals from the two phase detectors to determine phase angles thereof indicative of whether the defect is on an inner surface or an outer surface and of the depth of the defect, and a recorder for separately recording signals from the arithmetic processing unit which are representative of the defect on the inner surface and the depth thereof or the defect on the outer surface and the depth thereof.

10 Claims, 15 Drawing Figures

① WOBBLING (NOISE)
② CONCAVE (PROJECTION ON INNER SURFACE)
③ CRACK IN INNER SURFACE (1/4 t)
④ CRACK IN INNER SURFACE (1/2 t)
⑤ DRILLED HOLE
⑥ CORROSION ON INNER SURFACE (ABOUT 1/2 t)
⑦ CRACK IN OUTER SURFACE (1/2 t)
⑧ CORROSION ON OUTER SURFACE (SHALLOW)
⑨ BUFFLE SUPPORT

EDDY CURRENT DEFECT-DETECTING SYSTEM FOR DETERMINING AN INNER OR OUTER DEFECT AND ITS DEPTH IN METAL TUBES

BACKGROUND OF THE INVENTION

The present invention relates to an eddy current defect-detecting system, and more particularly to an eddy current defect-detecting system for metal tubes which is capable of determining defects on inner and outer surfaces and detecting the depth of a defect based on the phase of a flaw or defect of a defect signal which phase varies with the conditions of the defect formed on a metal tube, that is, the location and depth of the defect.

Prior eddy current defect-detecting systems have a test coil with a high-frequency current flowing therethrough. For defect detection, the test coil is inserted into a metal tube for electrically measuring a variation in the amplitude of an eddy current generated by a flaw (hereinafter referred to as a "defect") present on the metal tube. Since the variation in the eddy current (impedance variation) is quite small, it is amplified by a detector (hereinafter referred to as a "bridge") and an amplifier and then converted into a voltage. The signal includes a defect-indicative signal component and noise due to wobbling of the coil caused when the latter is inserted into the metal tube being tested. This test method is known as an amplitude method which indicates the shape and depth of a defect with one signal for evaluation of the defect.

However, the conventional eddy current defect-detecting systems fail to tell a defect with a large thickness reduction in a narrow area from a defect accompanying a small thickness reduction in a wide area, and hence are liable to judge a metal tube suffering only from a small thickness reduction and still usable as requiring replacement.

SUMMARY OF THE INVENTION

The above-described drawbacks in the prior art apparatus have been successfully eliminated by the present invention.

It is an object of the present invention to provide an eddy current defect-detecting system for metal tubes which is capable of measuring a defect on an outer or inner surface of a metal tube and the depth of the defect.

Another object of the present invention is to provide an eddy current defect-detecting system for metal tubes which is capable of accurately and quickly measuring a defect on an outer or inner surface of a metal tube and the depth of the defect.

To accomplish the above objects, an eddy current defect-detecting system for a metal tube according to the present invention comprises a detector including test coils movable axially through the metal tube for detecting as an impedance variation a variation in an eddy current produced due to a defect present in the metal tube, an oscillator for exciting the detector at a high frequency, a phase adjuster responsive to an oscillated output from the oscillator for adjusting the phase of the oscillated output to produce a first control signal, a phase shifter responsive to the first control signal from the phase adjuster for issuing a second control signal which is 90° out of phase with the first control signal, two phase detectors for producing a first defect signal by effecting first phase detection on an output signal from the detector with the first control signal and a second defect signal by effecting second phase detection on the output signal from the detector with the second control signal, an arithmetic processing unit for electrically reading amplitudes of the first and second defect signals from the two phase detectors to determine phase angles thereof indicative of whether the defect is on an inner surface or an outer surface and of the depth of the defect, and a recorder for separately recording signals from the arithmetic processing unit which are representative of the defect on the inner surface and the depth thereof or the defect on the outer surface and the depth thereof.

These and other objects of the invention will become apparent from the following description of an embodiment thereof when taken together with the drawings.

DETAILED DESCRIPTION OF THE PREFERRED EMBODIMENT

Figure 1:
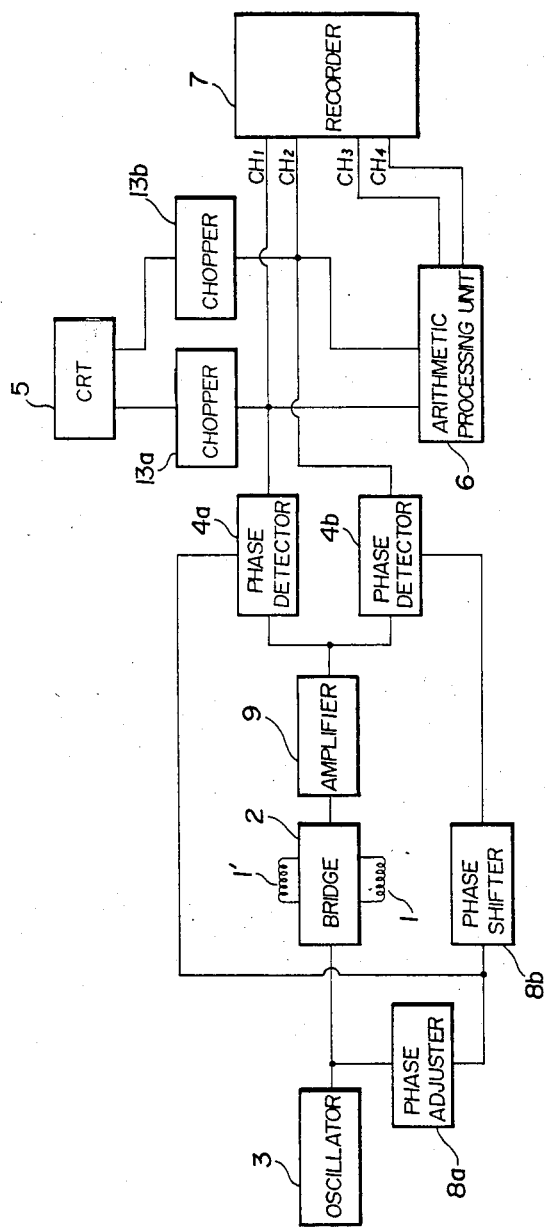
FIG. 1 is a block diagram of an eddy current defect-detecting system for metal tubes according to the present invention.
Figure 6:
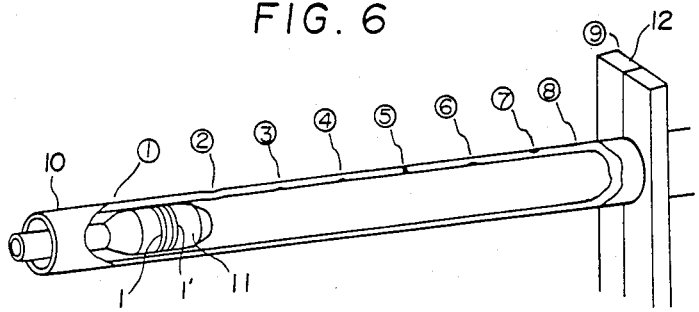
FIG. 6 is a diagram showing Lissajous figures illustrative of typical defect patterns produced by passing test coils through a metal tube.
Figure 10:
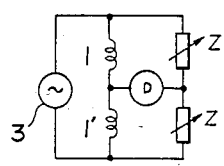
FIG. 10 is a circuit diagram of a bridge circxuit including test coils in the system of FIG. 1.

As shown in FIG. 1, an eddy current defect-detecting system according to a preferred embodiment of the present invention basically comprises a detector 2 including a pair of test coils 1, 1', an oscillator 3, a pair of phase detectors 4a, 4b, a picture display 5, an arithmetic processing unit 6, a recorder 7, a phase adjuster 8a, a phase shifter 8b, an amplifier 9, and choppers 13a, 13b. More specifically, as shown in FIG. 6, the test coils 1, 1' are wound around a probe 11 in axially juxtaposed relation and movable axially through a metal tube 10 being tested for detecting as an impedance variation a variation in an eddy current generated due to a defect or dent present in the metal tube 10. The detector 2 comprises a bridge including the test coils 1, 1' as illustrated in FIG. 10. The oscillator 3 is connected to the bridge 2 for exciting the bridge 2 at a high frequency such that an eddy current flows within the wall of the metal tube. The phase adjuster 8a is connected to the oscillator 3 and the bridge 2 and is responsive to an oscillated output from the oscillator 3 for adjusting its phase to produce a first control signal. The phase shifter 8b is connected to an output terminal of the phase adjuster 8a for producing a second control signal by shifting the phase of the first control signal by 90°. The amplifier 9 is connected to an output terminal of the bridge 2 and serves as a tuning amplifier for amplifying a signal of a required frequency only.

The phase detectors 4a, 4b are coupled to an output terminal of the amplifier 9 for producing a first defect signal or X-axis signal by effecting first phase detection on an output signal from the bridge 2 with the first control signal and a second defect signal or Y-axis signal by effecting second phase detection on the output signal from the bridge 2 with the second control signal which is 90° out of phase with the first control signal. The arithmetic processing unit 6 which is in the form of a central processing unit is coupled to output terminals of the phase detectors 4a, 4b for electrically reading amplitudes of the first and second defect signals from the phase detectors 4a, 4b to find phase angles thereof indicative of whether a detected defect is on an inner surface or an outer surface of the metal tube and of the depth of the defect. The recorder 7 which is of the multichannel type is connected to the phase detectors 4a, 4b and the arithmetic processing unit 6 for recording a defect on an inner surface (hereinafter referred to as an "inner defect") and its depth and a defect on an outer surface (hereinafter referred to as an "outer defect") and its depth. The choppers 13a, 13b are connected to the output terminals, respectively, of the phase detectors 4a, 4b for converting the issued defect signals into AC signals of a fixed frequency having amplitudes proportional to the magnitudes of the defect signals. The picture display 5 comprises a cathode-ray tube 5 coupled to output terminals of the choppers 13a, 13b and having X- and Y-axis input terminals receptive of output signals from the choppers 13a, 13b for displaying defect patterns as Lissajous figures on the screen.

Figure 2A:
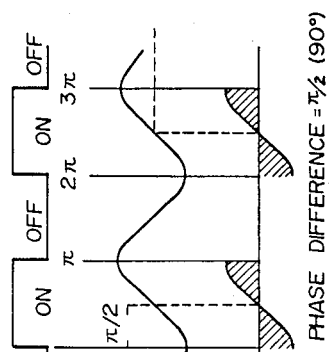
FIG. 2(a) is a timing chart showing signal waveforms generated when a control signal and an input signal has a phase difference $\phi$ in a phase detector in the system shown in FIG. 1.
Figure 2B:
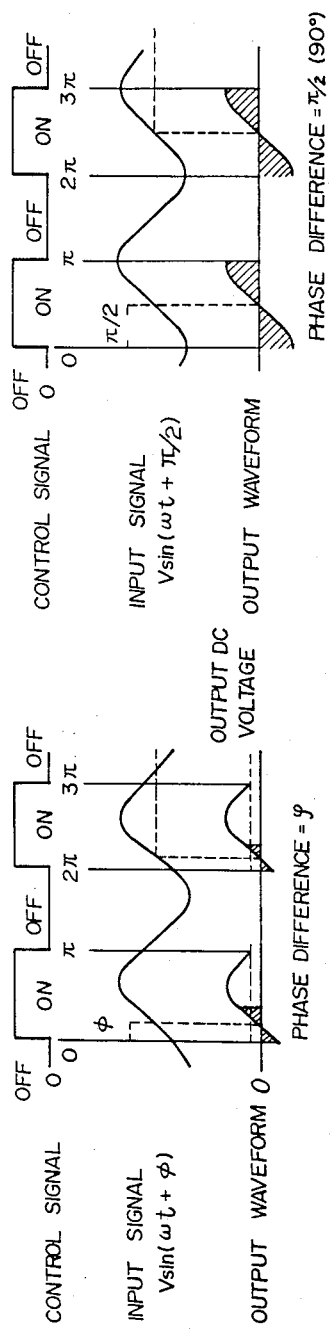
FIG. 2(b) is a timing chart similar to FIG. 2(a) showing signal waveformed produced when the phase difference is $\pi/2$.

Operation the eddy currrent defect-detecting system will be described in detail. An AC signal is supplied from the oscillator 3 (FIG. 1) to the bridge 2, and impedances Z (FIG. 10) in the bridge 2 are varied to balance the latter. The test coils 1, 1' which are wound around the probes 11 movable axially through the metal tube being tested as shown in FIGS. 1 and 6 coact with an eddy current generated in the metal tube 10, and vary their impedance dependent on the condition of the metal tube 10. The impedance variation of the test coils 1, 1' is converted by the bridge 2 into an electric signal which is issued through its output terminal. The test frequency is determined by the bridge 2 and selected taking into account a skin effect (penetration depth), defects and other factors. Stated otherwise, a test frequency should be selected which is optimum for the test speed, the material of the metal tube, and the relationship between the shape and dimensions of the metal tube and the penetration depth. To allow selection of desired freqquencies, the oscillator 3 is of the variable-frequency type generally comprising a CR oscillator or a crystal oscillator. The output signal from the bridge 2 is delivered through the amplifier 9 to the phase detectors 4a, 4b. While various designs are available of the phase detectors 4a, 4b, those employing electronic switching circuits are generally used. As shown in FIG. 2(a), the phase detectors 4a, 4b are energized by the control signals to allow the input signals to appear as output signals during a half period in which the phase of the control signals ranges from 0 to $\pi$. During another half period in which the control signals have a phase in the range of from $\pi$ to $2\pi$, the phase detectors 4a, 4b are de-energized to disable their output terminals. When signals which are $\phi$ out of phase with the control signals are applied to the input terminals of the phase detectors 4a, 4b, they produce an output waveform as shown in FIG. 2(a). By averaging this output waveform, hatched portions are cancelled out by each other, and the remaining portion becomes a DC voltage as shown by the broken line. When the input signals are $\pi/2$ (90°) out of phase with the control signals as illustrated in FIG. 2(b), the output signals have a waveform symmetrical with respect to the horizontal axis. With this output waveform averaged, no voltage appears on the output terminals of the phase detectors 4a, 4b.

The DC output voltages from the phase detectors 4a, 4b will now be derived by using mathematical formulas. Assuming that the input signals are $\phi$ out of phase with the control signals which give a phase reference, the input signals are expressed by $2V \sin(\omega t + \phi)$, and the DC voltage E obtained by averaging the outputs from the phase detectors 4a, 4b can be expressed as follows:

$$E = \frac{1}{T} \int_0^{T/2} \sqrt{2} \, V\sin(\omega t + \phi) dt = \frac{\sqrt{2} \, V}{\pi} \cos\phi \qquad (1)$$

where $T = 1/f$, $\omega = 2\pi f = 2\pi/T$, f: frequency, $\omega$:angular frequency, T: period Therefore, the output DC voltages from the phase detectors 4a, 4b are proportional to the voltage V of the input signals and the cosine of the phase $\phi$ of the input signals with respect to the reference phase of the control signals.

Figure 3:
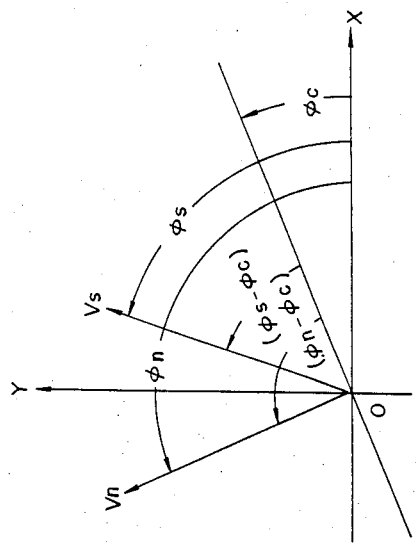
FIG. 3 is a vector diagram illustrative of signals in the phase detector.

In the vector diagram of FIG. 3, let the voltage of a signal produced by a defect be Vs, the phase thereof be $\phi$s, the voltage of a signal caused by vibrations due to the movement of the coil detector in the metal tube (wobbling of the test coils as they move through the metal tube) be Vn, and the phase thereof be $\phi$n. It is assumed that the phase c of the control signals can be selected as desired by the phase adjuster 8a. The two input signals have respective phases ($\phi$s−$\phi$c), ($\phi$n−$\phi$c) with respect to the reference phase of the control signals. When these two input signals are applied simultaneously to the phase detectors 4a, 4b, the DC voltage of the output signals is derived from the equation (1) as follows:

$$E = \frac{\sqrt{2}}{\pi} \{Vs\cos(\phi s - \phi c) + Vn\cos(\phi n - \phi c)\} \qquad (2)$$

When the phase $\phi$c of the control signals is varied by the phase adjuster 8a so as to be:

$$\phi n - \phi c = \pi/2 \qquad (3)$$

then, $\cos(\phi n - \phi c) = 0$, and the following results:

$$E = \frac{\sqrt{2}}{\pi} \cos(\phi s - \phi c) \qquad (4)$$

irrespectively of the value of the voltage Vn. By thus adjusting the phase $\phi c$ of the control signals with the phase adjuster 8a so that the equation (3) can be met, the signal caused by the vibrations due to the movement of the coil detector can be suppressed to allow only a defect-dependent signal to be detected as indicated by the equation (4). The phase shifter 8b produces the second control signal which is 90° out of phase with the first control signal for the control of the phase detector 4b in order to generate the first and second defect signals separately.

Figure 11:
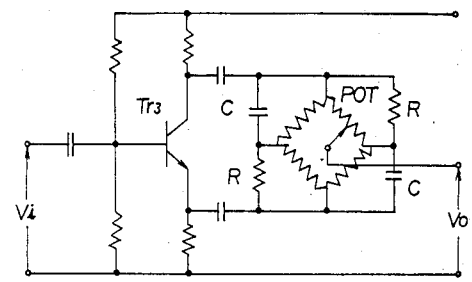
FIG. 11 is a circuit diagram of a phase shifter and a phase adjuster in the system of FIG. 1.

In actual defect-detecting tests, the tube being tested is moved and the phase adjuster 8a is adjusted to minimize indications on the testing device which would result from vibrations due to movement thereof for determining the phase of the control signals. The phase adjuster 8a is used in the eddy current defect detector for selecting the phase of the control signals for the phase detectors 4a, 4b as desired. As illustrated in FIG. 11, the phase shifter 8b and the phase adjuster 8a generally comprise a CR phase shifting circuit in actual use. This circuit has a phase selection knob for rotating a potentiometer POT.

Figure 12:
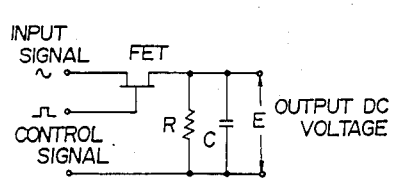
FIG. 12 is a circuit diagram of a phase detector in the system of FIG. 1.

FIG. 12 illustrates a circuit arrangement for the phase detectors 4a, 4b by way of example. The circuit comprises a phase detector including a series-connected switch in the form of a bidirectional field-effect transistor FET. When a positive pulse is applied as a control signal, the field effect transistor is rendered conductive to allow an input signal to appear as an output signal. When a negative control signal output is applied, the field-effect transistor is cut off to produce no output signal. A capacitor C is connected across output terminals to average the output signal.

By operating the phase adjuster 8a and the phase detectors 4a, 4b in the foregoing manner, X- and Y-axis signals serving as defect signals are issued from the phase detectors 4a, 4b, respectively. These signals are applied through the choppers 13a, 13b to the cathode-ray tube 5. The cathode-ray tube 5 displays output signals from the choppers 13a, 13b in the form of vectors and is used when observing defect signals and other noise phase relationships. The images on the cathode-ray tube 5 are displayed as Lissajous figures including straight lines and ellipses.

Figure 13:
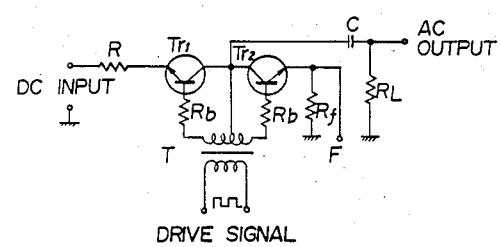
FIG. 13 is a circuit diagram of a transistor chopper in the system of FIG. 1.

As shown in FIG. 13, each of the choppers 13a, 13b includes a pair of transistors Tr1, Tr2 having bases to which a drive signal is applied to turn on and off the junctions between emitters and collectors. Thus, the choppers 13a, 13b serve as switches intermittently energizable dependent on the drive frequency for generating an AC output.

Figure 4A:
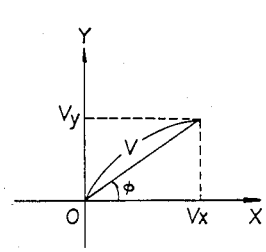
FIGS. 4(a) and 4(b) are vector diagrams of a signal with its phase advanced by $\phi$ with respect to a phase reference signal (X axis) and a signal produced by effecting phase detection on the above signal.

As illustrated in FIG. 4(a), a signal V having a phase advanced by $\phi$ with respect to a signal (X axis) giving a phase reference can be broken into a reference signal component Vx and a component Vy advanced in phase by 90°. At this time, the following relationship exists between these components:

$$\left. \begin{array}{l} Vx = V\cos\phi \\ Vy = V\sin\phi \end{array} \right\} \qquad (5)$$

When the signal V is detected by using the two phase detectors 4a, 4b with their control signals being 90° ($\pi/2$) out of phase with each other by means of the phase shifter 8b, the phase detectors 4a, 4b produce output DC voltage signals which are expressed from the equation (1) as follows:

$$\left. \begin{array}{l} Ex = \dfrac{\sqrt{2}\,V}{\pi} \cos\phi \\ Ey = \dfrac{\sqrt{2}\,V}{\pi} \cos(\phi - \pi/2) = \dfrac{\sqrt{2}\,V}{\pi} \sin\phi \end{array} \right\} \qquad (6)$$

Figure 4B:
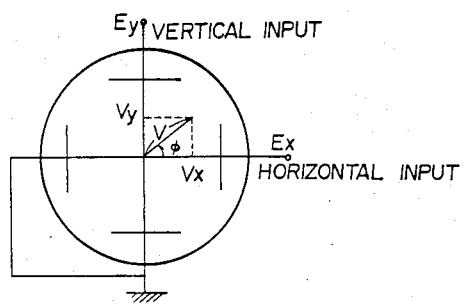
Figure 5:
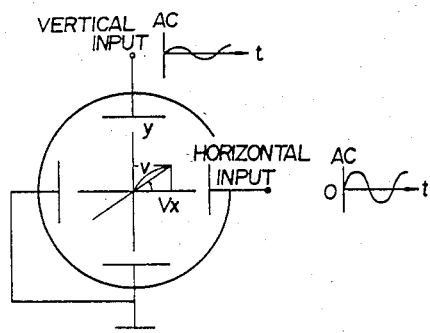
FIG. 5 is a diagram showing a Lissajous figure displayed when out-of-phase signals are applied to horizontal and vertical input terminals of a CRT.

It is understood from the equations (5) and (6) that the voltages Ex, Ey are proportional respectively to the components Vx, Vy. By applying the DC voltages Ex, Ey to the horizontal and vertical input terminals of the cathode-ray tube 5, the bright spot thereon which moves in proportion to the input voltage displays the signal voltage V as a vector as shown in FIG. 4(b). When the phases of the control signals for the two phase detectors 4a, 4b employed to generate the voltages Ex, Ey are varied while keeping the phases 90° out of phase by means of the phase shifter 8b, the phase $\phi$ shown in FIG. 4(a) is also varied. Accordingly, the voltages Ex, Ey also changes as is apparent from the equations (6). Accordingly, the DC voltages Ex, Ey generated by the phase detectors 4a, 4b are converted by the choppers 13a, 13b into AC signals which are then applied to the horizontal and vertical input terminals of the cathode-ray tube 5. The spot on the cathode-raty tube 5 varies in position with time, and displays the input signals a straight line as shown in FIG. 5. The angle formed between the displayed straight line and the X axis indicates the phase, and the length of the line indicates the magnitude of the signals. When the AC signals applied to the horizontal and vertical input terminals are out of phase with each other, the signals are displayed as an ellipse. As a consequence, Lissajous figures can be displayed as illustrated in FIG. 6 when the X- and Y-axis signals are applied to the horizontal and vertical input terminals of the cathode-ray tube 5. In reality, the inclination of a displayed Lissajous figure, that is, the phase, permits determination as to whether a defect is an inner defect or an outer defect, and detection of the depth of the defect. More specifically, when the phase is in the range of from 0° to 45°, the defect is an inner defect; when the phase is in the vicinity of 45°, the defect is a through hole; and when the phase ranges from 45° to 180°, the defect is an outer defect.

Figure 7:
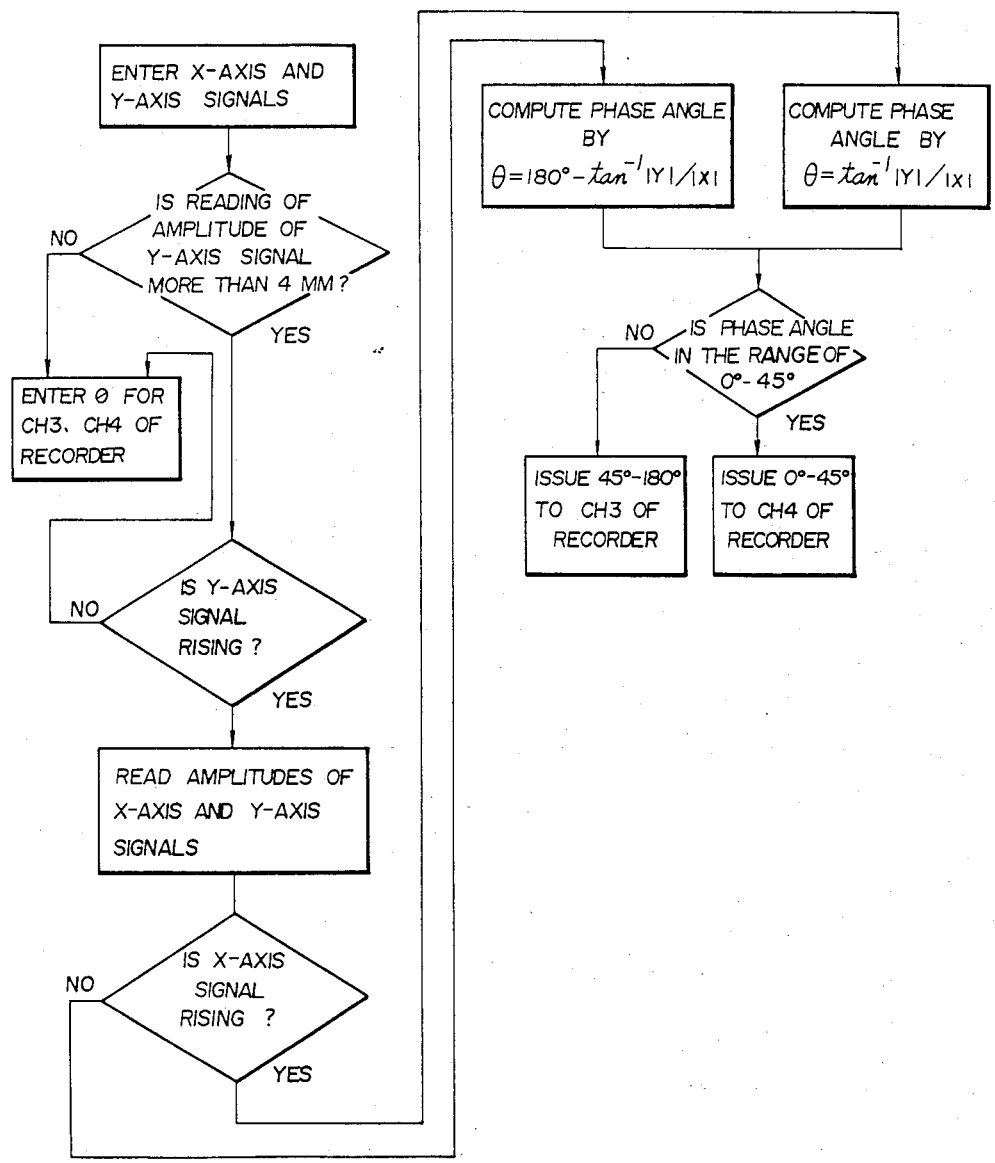
FIG. 7 is a flowchart of the steps of processing operation of an arithmetic processing unit.
Figure 8:
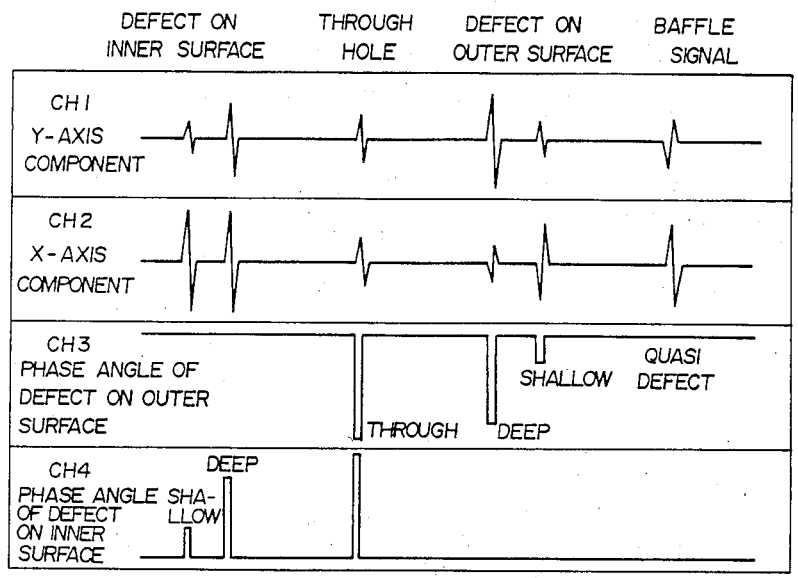
FIG. 8 is a diagram showing a defect on an inner surface and its depth and a defect on an outer surface and its depth as indicated on a recording sheet in a recorder.

FIG. 7 shows the steps of processing operation of the arithmetic processing unit 6. First, X- and Y-axis signals from the two phase detectors 4a, 4b are applied to the arithmetic processing unit 6. If the amplitude of the Y-axis signal is 4 mm or more, then the arithmetic processing unit 6 determines the phase of the Y-axis siganl. At this time, if a half amplitude of the Y-axis signal is 2 mm or more, then the arithmetic processing unit 6 determines whether the Y-axis signal is positive or negative. No output is issued for channels 3 and 4 of the recorder 7 if the signal has a Y-axis amplitude below the above level. This is because the recording level is selected taking noise into account. Only when the Y-axis signal is rising, the phase of the X-axis signal and the amplitudes of the X- and Y-axis signals are read by the arithmetic processing unit 6. The phase angle is computed according to the equation $\theta = \tan^{-1} |Y|/|X|$ or $\theta = 180° - \tan^{-1} |Y|/|X|$. If the phase angle is in the range of from 0° to 45°, then the arithmetic processing unit 6 judges the defect as an inner defect and issues an output proportional to the phase angle with 0° and 45° as zero and full-scale readings to a channel 4 of the recorder 7. If the phase angle ranges from 45° to 180°, the defect is judged as an outer defect, and an output proportional to the phase angle with 180° and 45° as zero and full-scale readings is issued to a channel 3 of the recorder 7. The depth of the defect can be measured at this time by a phase angle difference. When the defect is a through hole, an output is applied to both the channels 3 and 4 of the recorder 7. The output mode is selected so that it matches defect images. The result of measurement is recorded in the format shown in FIG. 8 on the recorder 7, which comprises a pen recorder.

Figure 9:
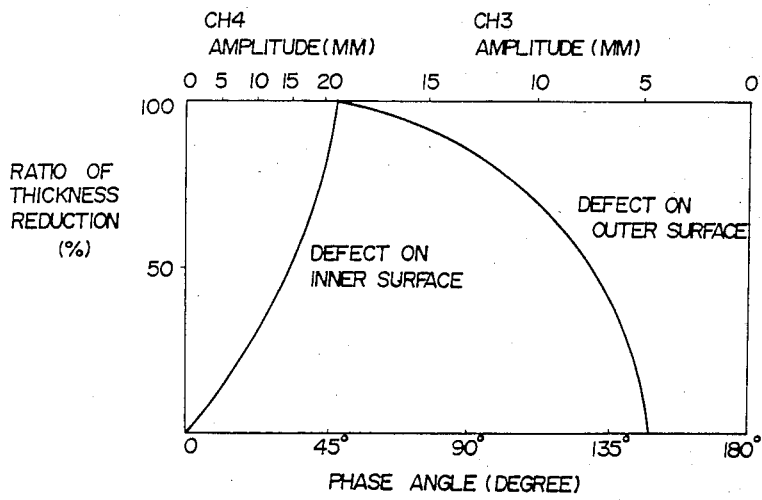
FIG. 9 is a diagram illustrative of calibration curves showing the ratio of thickness reduction with respect to a phase angle.

It will be understood from the calibration curves of FIG. 9 that any defect can be determined as an inner defect or an outer defect and the raio of thickness reduction an be measured by reading the phase angle on the cathode-ray tube 5, and also by the used channel (channel 3 or channel 4) of the recorder 7 and the amplitude (mm) of a recorded signal thereon.

Experiments indicate that an estimated ratio of thickness reduction measured of a metal tube by the system of the invention suffered only from errors in the range of ±10% of an acually measured ratio of thickness reduction. Automatic analysis of phase angles using the arithmetic processing unit without manual intervention permitted easy and quick determination of an inner or outer defect and computation of the depth of the defect, required a reduced period of time for testing, and resulted in improved testing dependability.

Thus, there is provided in accordance with the invention an eddy current defect-detecting system for metal tubes which has the advantage discussed above. The embodiment described is intended to be merely exemplary and those skilled in the art will be able to make variations and modifications in them without departing from the spirit and scope of the invention. All such modifications and variations are contemplated as falling within the scope of the claims.

What is claimed is:

1. An eddy current defect-detecting system for a metal tube, comprising:
  (a) a detector including test coil means movable axially through the metal tube for detecting as an impedance variation a variation in an eddy current produced due to a defect present in the metal tube;
  (b) an oscillator exciting said detector at a high frequency;
  (c) a phase adjuster responsive to an oscillated output from said oscillator for adjusting the phase of the oscillated output to produce a first control signal;
  (d) a phase shifter responsive to said first control signal from said phase adjuster for issuing a second control signal which is 90° out of phase with said first control signal;
  (e) two phase detectors for producing a first X-axis defect signal by effecting first phase detection on an output signal from said detector with said first control signal and a second Y-axis defect signal by effecting second phase detection on the output signal from said detector with said second control signal;
  (f) an arithmetic processing unit for electrically reading amplitudes of said first and second defects signals from said two phase detectors to determine phase angles thereof indicative of whether the defect is on an inner surface or an outer surface and of the depth of the defect, said arithmetic processing unit determining the phase angle $\theta$ of said Y-axis signal when the amplitude of said Y-axis signal exceeds a predetermined value and said arithmetic processing unit determining whether said Y-axis signal is positive or negative when a half amplitude of the Y-axis signal is at least half of said predetermined value, said phase angle $\theta = \tan^{-1} |Y|/|X|$ or $\theta = 180° - \tan^{-1} |Y|/|X|$, a calculated phase angle in a first range indicating that the defect is on an inner surface and a phase angle in a second range, different from said first range, indicating that the defect is on an outer surface, said arithmetic processing unit providing a first defect-indicating output signal proportional to the calculated phase angle when an inner surface defect is detected and providing a second defect-indicating output signal proportional to the calculated phase angle when an outer surface defect is detected; and
  (g) recorder means for separately recording signals from said arithmetic processing unit which are representative of the defect on the inner surface and the depth thereof or the defect on the outer surface and the depth thereof, said first defect-indicating output signal being issued to one channel of said recorder means and said second defect-indicating output signal being issued to a second channel of said recorder means.

2. An eddy current defect-detecting system according to claim 1, including a probe movable axially through the metal tube being tested, said test coil means being wound around said probe.

3. An eddy current defect-detecting system according to claim 2, wherein said test coil means comprises a pair of test coils wound around said probe in axially juxtaposed relation.

4. An eddy current defect-detecting system according to claim 1, wherein said detector comprises a bridge circuit.

5. An eddy current defect-detecting system according to claim 1, wherein said oscillator comprises a variable-frequency oscillator for producing a test frequency optimum for the material, shape and dimensions of the metal tube being tested.

6. An eddy current defect-detecting system according to claim 1, wherein said two phase detectors comprises detectors controlled by said phase adjuster.

7. An eddy current defect-detecting system according to claim 1, wherein said arithmetic processing unit comprises a central processing unit for determining whether the defect present in the metal tube is on an inner surface thereof or an outer surface and for computing the depth of the defect.

8. An eddy current defect-detecting system according to claim 1, wherein said recorder means comprises a multichannel recorder for separately recording a defect on an inner surface of the metal tube and the depth thereof and a defect on an outer surface of the metal tube and the depth thereof.

9. An eddy current defect-detecting system for a metal tube, comprising:

(a) a detector including test coil means movable axially through the metal tube for detecting as an impedance variation a variation in an eddy current produced due to a defect present in the metal tube;

(b) an oscillator for exciting said detector at a high frequency;

(c) a phase adjuster responsive to an oscillated output from said oscillator for adjusting the phase of the oscillated output to produce a first control signal;

(d) a phase shifter responsive to said first control signal from said phase adjuster for issuing a second control signal which is 90° out of phase with said first control signal;

(e) two phase detectors for producing a first X-axis defect signal by effecting first phase detection on an output signal from said detector with said first control signal and a second Y-axis defect signal by effecting second phase detection on the output signal from said detector with said second control signal;

(f) two choppers for converting said first and second defect signals, respectively, from said phase detectors into AC signals of a fixed frequency having amplitude proportional to the magnitudes of said defect signals;

(g) a picture display responsive to the AC signals from said two choppers for displaying a defect pattern as a Lissajous figure on a screen thereof;

(h) an arithmetic processing unit for electrically reading amplitudes of said first and second defect signals from said two phase detectors to determine phase angles thereof indicative of whether the defect is on an inner surface or an outer surface and of the depth of the defect said arithmetic processing unit determining the phase angle ? of said Y-axis signal when the amplitude of said Y-axis signal exceeds a predetermined value and said arithmetic processing unit determining whether said Y-axis signal is positive or negative when a half amplitude of the Y-axis signal is at least half of said predetermined value, said phase angle $\theta = \tan^{-1} |Y|/|X|$ or $\theta = 180° - \tan^{-1} |Y|/|X|$, a phase angle in a first range indicating that the defect is on an inner surface and a phase angle in a second range, different from said first range, indicating that the defect is on an outer surface, said arithmetic processing unit providing a first defect-indicating output signal proportional to the calculated phase angle when an inner surface defect is detected and providing a second defect-indicating output signal proportional to the calculated phase angle when an outer surface defect is detected; and (i) recorder means for separately recording signals from said arithmetic processing unit which are representative of the defect on the inner surface and the depth thereof and the defect on the outer surface and the depth thereof, said first defect-indicating output signal being issued to one channel of said recorder means, said second defect-indicating output signal being issued to a second channel of said recorder means.

10. An eddy current defect-detecting system according to claim 9, wherein said picture display comprises a cathode-ray tube having horizontal and vertical input terminals receptive of said first and second defect signals from said phase detectors, respectively.

* * * * *

UNITED STATES PATENT AND TRADEMARK OFFICE
CERTIFICATE OF CORRECTION

PATENT NO. : 4,628,260

DATED : December 9, 1986

INVENTOR(S) : Sanshiro KIMOTO, Hisao KOKUBO, Yasunobu YAMABAYASHI, and Kenichi HIDEJIMA It is certified that error appears in the above—identified patent and that said Letters Patent is hereby corrected as shown below:

Column 7, line 56 (claim 1, line 7) after "oscillator" insert --for--.

Column 9, line 22 (claim 9, line 24) "amplitude" should read --amplitudes--.

Column 10, line 1 (claim 9, line 35) "?" should read -- $\theta$ --.

Signed and Sealed this

Eleventh Day of August, 1987

*Attest:*

DONALD J. QUIGG

*Attesting Officer*      *Commissioner of Patents and Trademarks*